(12) United States Patent
Pellacini et al.

(10) Patent No.: US 6,455,576 B1
(45) Date of Patent: Sep. 24, 2002

(54) MACROLIDES WITH ANTI-INFLAMMATORY ACTIVITY

(75) Inventors: Franco Pellacini, Milan; Daniela Botta, Como; Stefano Romagnano, Buccinasco; Ermanno Moriggi, Busto Arsizio; Lorenzo Pradella, Cernusco sul Naviglio, all of (IT)

(73) Assignee: Zambon Group S.p.A., Venice (IT)

( * ) Notice: Subject to any disclaimer, the term of this patent is extended or adjusted under 35 U.S.C. 154(b) by 0 days.

(21) Appl. No.: 09/889,284

(22) PCT Filed: Jan. 12, 2001

(86) PCT No.: PCT/EP00/00163

§ 371 (c)(1), (2), (4) Date: Sep. 5, 2001

(87) PCT Pub. No.: WO00/42055

PCT Pub. Date: Jul. 20, 2000

(30) Foreign Application Priority Data

Jan. 15, 1999 (IT) .......................................... MI99A0061

(51) Int. Cl.⁷ ............................................. A61K 31/335
(52) U.S. Cl. ...................................... 514/450; 549/267
(58) Field of Search ........................... 549/267; 514/450

(56) References Cited

U.S. PATENT DOCUMENTS 3,928,387 A    12/1975    Kierstead et al. ....... 260/210 E

FOREIGN PATENT DOCUMENTS

EP    0 096 013    12/1983
EP    0 254 534    1/1988

OTHER PUBLICATIONS

Robinson, W. S. 'Preparation of erythromycin derivatives and their pharmaceutical compositions for inhibiting virus replicaiton and disease' CA 110:39320 (1989).*

Ronald A. LeMahieu, et al., Journal of Medicinal Chemistry, vol. 17, No. 9, pp. 953–956, "Glycoside Cleavage Reactions on Erythromycin A. Preparation of Erythronolide A", 1974.

* cited by examiner

*Primary Examiner*—Amelia Owens
(74) *Attorney, Agent, or Firm*—Oblon, Spivak, McClelland, Maier & Neustadt, P.C.

(57) ABSTRACT

3'-Des-dimethylamino-9-oxyimino macrolides of formula (I) endowed with anti-inflammatory activity and their pharmaceutical use are described.

10 Claims, No Drawings

MACROLIDES WITH ANTI-INFLAMMATORY ACTIVITY

The present invention relates to macrolides with anti-inflammatory activity and, more particularly, it relates to des-dimethylamino macrolide derivatives with anti-inflammatory activity, their pharmaceutically acceptable salts and pharmaceutical compositions containing them as active ingredients.

It is known that many antibiotics, in particular the class of macrolides with 14 atoms derived from erythromycin, are endowed with anti-inflammatory properties in addition to the antibacterial activity [Clin. Immunother., (1996), 6, 454–464].

Erythromycin is a natural macrolide (The Merck Index, XII edition, n° 3720, page 625) that has had a very broad clinical use in the treatment of infections caused by Gram-positive bacteria, by some Gram-negative ones or by Mycoplasma.

Recently the interest of the scientific community has been focused on the anti-inflammatory and immunomodulatory component of erythromycin and derivatives [Journal of Antimicrobial Chemotherapy, (1998), 41, Suppl.B, 37–46].

Such activity is well documented by both clinical studies and in vivo and in vitro experiments.

For example, macrolides have proved to be effective in the therapy of inflammatory diseases such as panbronchiolitis [Thorax, (1997), 52, 915–918], bronchial asthma [Chest, (1991), 99, 670–673] and cystic fibrosis [The Lancet, (1998), 351, 420], or in animal models of inflammation such as, for example, the zymosan-induced peritonitis in mice [Journal of Antimicrobial Chemotherapy, (1992), 30, 339–348] and the neutrophil recruitment induced by endotoxin in rat trachea [Antimicrobial Agents and Chemotherapy, (1994), 38, 1641–1643] or in in vitro studies on immune system cells, such as neutrophils [The journal of Immunology, (1997), 159, 3395–4005] and T-lymphocytes [Life Sciences, (1992), 51, PL 231–236] or in the modulation of cytokines, such as interleukin 8 (IL-8) [Am. J. Respir. Crit. Care Med., (1997), 156, 266–271] or interleukin 5 (IL-5) (EP 0 775 489 and EP 0 771 564, Taisho Pharmaceutical Co., Ltd).

The peculiar therapeutic efficacy of macrolides on diseases in which the conventional anti-inflammatory drugs, such as for example corticosteroids, have demonstrated to be ineffective [Thorax, (1997), 52, 915–918, already cited] justifies the high interest towards this new potential class of anti-inflammatories.

Nevertheless the strong antibacterial activity of the conventional macrolides does not allow an enlarged use in the chronic treatment of inflammatory processes not due to pathogens because of the rapid onset of resistant strains.

Therefore, it would be desirable to have new substances with a macrolide structure that show anti-inflammatory activities and, in the mean time, that are devoid of antibiotic properties.

For a greater clarity we show the formula of erythromycin in which the numbering adopted in the present patent application is indicated.

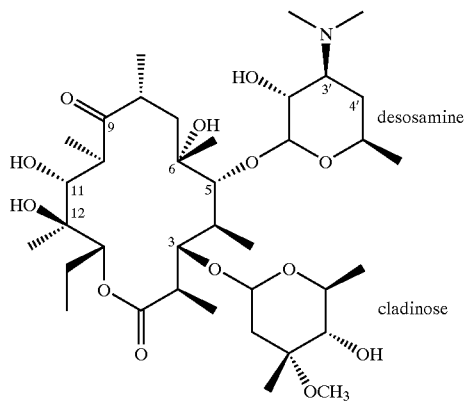

Some classes of erythromycin derivatives endowed with a high anti-inflammatory activity are described in the literature.

For example, in the already cited European patent applications in the name of Taisho derivatives of erythromycin modified at 3, 9, 11 and 12 position, as strong inhibitors of the synthesis of IL-5 are claimed.

N-alkyl derivatives of azithromycin, without cladinose and desosamine, of formula

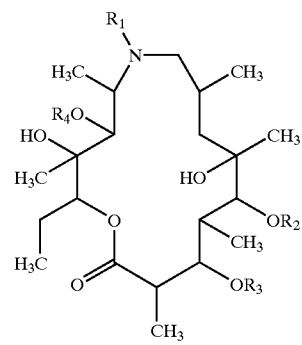

wherein $R_1$ is hydrogen, a lower alkyl or a lower alkanoyl; $R_2$, $R_3$ and $R_4$, the same or different, are hydrogen or a lower alkanoyl; are described as anti-inflammatories in EP 0 283 055 (Sour Pliva).

The use of erythromycin as anti-inflammatory that acts by reducing the release of interleukin 1 through the inhibition of the mammalian mdr-P glycoprotein is claimed WO 92/16226 in the name of Smith-Kline Beecham Corporation.

Among the macrolide derivatives described in the literature a few are 3'-desdimethylamino-9-oxyimino derivatives. The limited interest towards this class of compounds is justified by the fact that the relevance of the dimethylamino group for the activity of ribosomal binding typical of macrolides is known [Tetrahedron Letters, (1994), 35, 3837–3840].

In U.S. Pat. No. 3,928,387 (Hoffmann-La Roche Inc.) 3'-desdimethylamino-3',4'-dehydroerythromycin A oxime is described, as intermediate useful for the preparation of the antibiotic 1745A/X.

In EP 0 254 534 (Robinson, William S.) a very broad class of macrolides with antiviral activity is claimed. Among them the compound of formula whose correct chemical name is 3'-desdimethylamino-3',4'-dehydroerythromycin A 9-O-methyloxime notwithstanding in the text of EP 0 254 534 is erroneously reported as des-dimethylaminoerythromycin 9-O-methyloxime (page 10, line 46) is described.

Now we have found that by removing the dimethylamino group from the 3' position of desosamine of 9-oxyimino macrolides, compounds endowed with anti-inflammatory activity and essentially devoid of antibiotic properties are obtained.

Therefore, object of the present invention are compounds of formula (I)

wherein
R is hydrogen or methyl;
$R_1$ and $R_2$ are both hydrogen or they together form a bond;
$R_3$ is hydrogen, a linear or branched $C_1$–$C_5$ alkyl group, a benzyl group, optionally substituted by one or more substituents selected among nitro groups, hydroxy groups, carboxylic groups, amino groups, linear or branched $C_1$–$C_5$ alkyl groups, $C_1$–$C_4$ alkoxycarbonyl groups, aminocarbonyl groups or ciano groups, or a chain of formula $$\diagdown_{(CH_2)_r}\diagup^{X}\diagdown_{(CH_2)_m}\diagup^{X}\diagdown_{(CH_2)_n}\diagup^{A}$$

wherein
A is hydrogen or a phenyl group optionally substituted by one or two substituents selected among nitro groups, hydroxy groups, carboxylic groups, amino groups, linear or branched $C_1$–$C_5$ alkyl groups, $C_1$–$C_4$ alkoxycarbonyl groups, aminocarbonyl groups or ciano groups, or a 5 or 6 membered heterocycle, saturated or unsaturated, containing from 1 to 3 heteroatoms selected among nitrogen, oxygen and sulphur, optionally substituted by one or two substituents selected among $C_1$–$C_5$ alkyl groups, phenyl groups, hydroxy groups, oxo (=O) groups, nitro groups, $C_1$–$C_4$ alkoxycarbonyl groups, aminocarbonyl groups, mono or di-$C_1$–$C_4$-alkylaminocarbonyl groups, $C_1$–$C_4$-alkylcarbonyl groups;
X and Y, the same or different, are O, S, SO, $SO_2$ or $NR_4$, in which $R_4$ is hydrogen, a linear or branched $C_1$–$C_5$ alkyl group, a $C_1$–$C_5$ alkoxycarbonyl group, a benzyloxycarbonyl group;
r is an integer from 1 to 6;
m is an integer from 1 to 8;
n is an integer from 0 to 2;
and their pharmaceutically acceptable salts; the compounds 3'-desdimethylamino-3',4'-dehydroerythromycin A oxime ($R_1$ and $R_2$=bond; R=H; $R_3$=H) and 3'-desdimethylamino-3',4'-dehydroerythromycin A 9-O-methyloxime ($R_1$ and $R_2$=bond; R=H; $R_3$=$CH_3$) being excluded.

A further object of the present invention is the use of the compounds 3'-desdimethylamino-3',4'-dehydroerythromycin A oxime and 3'-desdimethylamino-3',4'-dehydroerythromycin A 9-O-methyloxime as anti-inflammatories.

The compounds of formula I are anti-inflammatory macrolides devoid of antibiotic activity and therefore they are useful in the treatment of inflammatory diseases.

With the term linear or branched $C_1$–$C_5$ alkyl groups a group selected among methyl, ethyl, n-propyl, isopropyl, n-butyl, isobutyl, sec-butyl, tert-butyl, n-pentyl and isopentyl is meant. With the term 5 or 6 membered heterocycle, saturated or unsaturated, containing from 1 to 3 heteroatoms selected among nitrogen, oxygen and sulphur, heterocycles such as pyrrole, thiophene, furan, imidazole, pyrazole, thiazole, isothiazole, isoxazole, oxazole, pyridine, pyrazine, pyrimidine, pyridazine, triazole, thiadiazole and their partially o totally saturated forms are meant.

Preferred compounds of formula I are the compounds in which R, $R_1$ and $R_2$ are hydrogen.

Within this class the compounds in which $R_3$ is a chain of formula $$\diagdown_{(CH_2)_r}\diagup^{X}\diagdown_{(CH_2)_m}\diagup^{X}\diagdown_{(CH_2)_n}\diagup^{A}$$

wherein
X, Y, A, r, m and n have the already reported meanings are particularly preferred.

Even more preferred compounds are the compounds in which $R_3$ is a chain of formula $$\diagdown_{(CH_2)_r}\diagup^{X}\diagdown_{(CH_2)_m}\diagup^{X}\diagdown_{(CH_2)_n}\diagup^{A}$$

wherein
r is 2, m is 2 or 6, n is 1, Y is $NR_4$, X is O or $NR_4$, $R_4$ is hydrogen and A is phenyl or thiazolyl.

Examples of pharmaceutically acceptable salts of the compounds of formula (I) are the salts with organic or inorganic acids such as hydrochloric, hydrobromic, hydriodic, nitric, sulphuric, phosphoric, acetic, tartaric, citric, benzoic, succinic and glutaric acid.

The compounds of formula I, object of the present invention, are prepared by following a synthetic scheme which comprises (a) the removal of the dimethylamino group at 3' position and (b) the optional functionalisation of the oxime.

The removal of the dimethylamino group is performed by oxidation, pyrolisis and optional reduction, according to known methods. It is evident to the man skilled in the art that, in order to avoid interferences with the functional groups optionally present at $R_3$ substituent, the removal of the dimethylamino group will be preferably accomplished starting from intermediates of formula

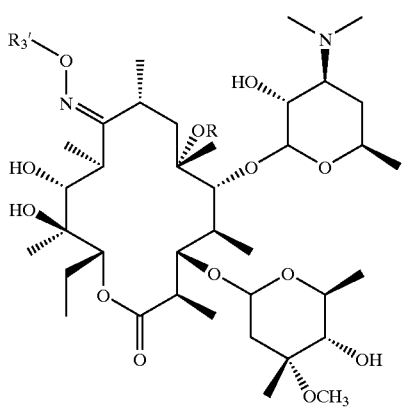

(II)

in which

R has the already reported meanings and $R_3'$ is hydrogen or a linear or branched $C_1$–$C_5$ alkyl group.

By oxidation the corresponding N-oxides of formula

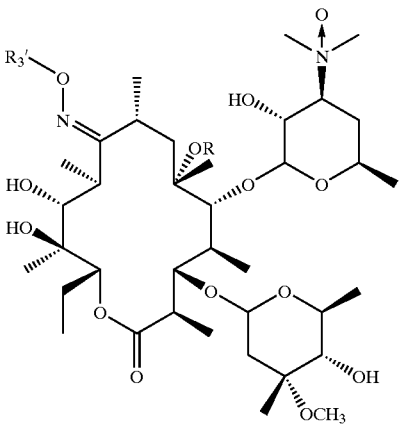

(III)

in which

R and $R_3'$ have the already reported meanings are obtained; that by pyrolisis, optionally followed by reduction, respectively give the compounds of formula

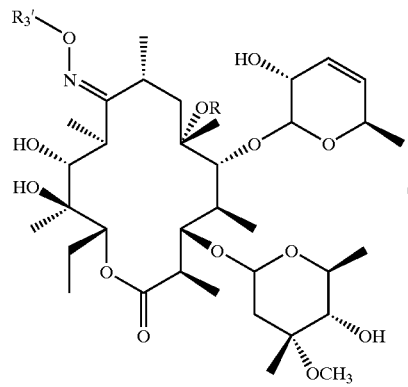

(I-A; $R_1$ and $R_2$ = bond)

and

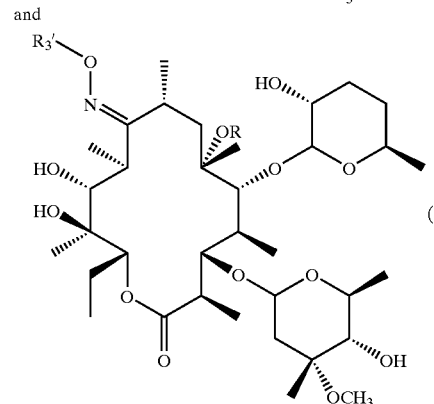

(I-B; $R_1$ = $R_2$ = H)

object of the present invention (I-$R_3$=hydrogen or $C_1$–$C_4$ alkyl).

According to common techniques, the compounds of formula I in which $R_3$ is different from hydrogen can be prepared from the compounds of formula I-A and I-B in which $R_3'$ is hydrogen by functionalisation of the oxime. Generally the functionalisation is carried out by reaction with a compound of formula $$R_3''-W \qquad (IV)$$

in which $R_3''$ has all the meanings of $R_3$ apart from hydrogen and W is a leaving group, preferably a chlorine or bromine atom or a mesyl group.

An alternative synthetic route particularly suited for the preparation of the compounds of formula I in which $R_3$ is a chain of formula

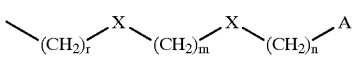

in which

X, Y, A, r, m and n have the already reported meanings; comprises the reaction of a compound of formula I in which $R_3$ is hydrogen with an intermediate of formula (V)

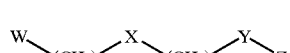

in which

W, X, Y, m and n have the already reported meanings and Z represents a protecting group;

to give the intermediate of formula

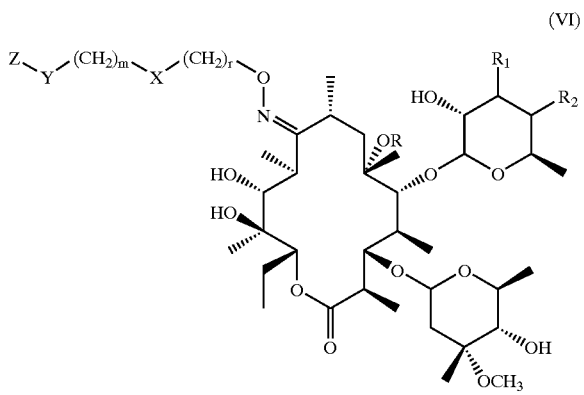

(VI)

in which R, $R_1$, $R_2$, X, Y, Z, r and m have the already reported meanings;
that after removal of the Z protecting group, is reacted with a derivative of formula

(VII)

in which A, W and n have the already reported meanings; to give the compounds of formula I.

The compounds of formula I in which Y is $NR_4$ can be prepared according to the above reported synthetic route also by using an aldehyde of formula

(VIII)

in which A has the already reported meanings;
in place of the intermediate of formula VII, subject to removal of the Z protecting group from the intermediate of formula VI.

Moreover, the compounds of formula I in which $R_1=R_2=H$ can be prepared by reduction of the corresponding compounds of formula I in which $R_1$ and $R_2$ form a bond.

The compounds of formula I, object of the present invention, are endowed with an anti-inflammatory activity and are devoid of antibiotic activity.

The pharmacological activity of the compounds of formula I has been evaluated by in vitro and in vivo tests in comparison with known macrolides, such as erythromycin, clarithromycin and roxithromycin, endowed with both anti-inflammatory activity and antibiotic activity.

The anti-inflammatory activity has been evaluated in vitro as inhibition of IL-8 release and of superoxide anion release (example 11) and in vivo as inhibition of LPS-induced neutrophilia after repeated administrations (example 12).

In all the experiments the compounds object of the present invention have resulted very active as anti-inflammatories and the anti-inflammatory activity has been equal to or greater than the one of the reference compounds.

For a therapeutical application the compound of formula I can be used in a pharmaceutical form suitable to oral or parenteral administration.

Therefore, object of the present invention are pharmaceutical compositions containing a therapeutically active amount of a compound of formula I or of a salt thereof in admixture with a pharmaceutically acceptable carrier.

With the aim to better illustrate the present invention the following examples are now given.

EXAMPLE 1

Preparation of [6-(2-hydroxy-ethylamino)-hexyl]-carbamic acid benzyl ester

To a solution of (6-hydroxy-hexyl)-carbamic acid benzyl ester (25 g; 99.47 mmoles), prepared as described in WO 96/18633, in $CH_2Cl_2$ (350 ml), cooled with ice at about 10° C., at first a solution of KBr (1.18 g; 9.94 mmoles) in water (20 ml) and TEMPO (0.155 g; 0.994 mmoles) and then, dropwise in about 15–20 minutes keeping the temperature at 10–12° C., a solution prepared with $NaHCO_3$ (7.5 g; 89.28 mmoles) and NaClO (4.5 % water solution; 197 ml; 125 mmoles) were added.

minutes after the end of the dripping, the phases were separated and the aqueous phase was extracted once with $CH_2Cl_2$ (100 ml). The collected organic extracts were washed twice with brine (20% NaCl) and dried on sodium sulphate.

3 Å molecular sieves (30 g) and then, by fast dropwise and by cooling with water and ice, a solution of 2-aminoethanol (35.9 ml; 0.597 moles) in ethanol (600 ml) were added to the obtained solution (about 800 ml).

Ended the dripping the mixture was kept under stirring at room temperature for 2 hours and then filtered.

$NaBH_4$ (4.54 g; 120 mmoles) was portionwise added to the obtained solution, cooled with water and ice, under stirring in a nitrogen atmosphere.

At the end of the addition, the reaction mixture was kept under stirring at room temperature for 2 hours and then the solvent was evaporated.

The residue was collected with water and ethyl acetate and the phases were separated, again extracting twice the aqueous phase with ethyl acetate.

The collected organic extracts were washed with brine (20% NaCl), dried on sodium sulphate and concentrated up to obtained an oily residue that was inclined to solidify.

The residue was triturated with hexane, filtered and washed with a mixture of hexane and ethyl ether, furnishing [6-(2-hydroxy-ethylamino)-hexyl]-carbamic acid benzyl ester (26.22 g; yield 89%) as a white solid.

$^1$H-NMR (200 MHz, $CDCl_3$) δ(ppm): 7.33–7.25 (m, 5H, Ar); 5.05 (s, 2H, $COOCH_2$); 4.96 (broad-t, 1H, NH); 3.63–3.58 (m, 2H, *$CH_2$—OH); 3.19–3.09 (m, 2H, $CH_2NCO$); 2.72–2.67 (m, N—*$CH_2$—$CH_2O$); 2.59–2.52 (m, 4H, OH and $CH_3$); 1.53–1.23 (m, 8H, 4$CH_2$).

EXAMPLE 2

Preparation of 6-(benzyloxycarbonylamino-hexyl)-(2-hydroxy-ethyl)-carbamic acid benzyl ester A solution of benzylchloroformate benzyl ester (50% in toluene, 42.5 ml; 0.128 moles) in ethyl acetate (85.5 ml) and 1N NaOH (128 ml, 0. 128 moles) were simultaneously dropwise added to a solution of [6-(2-hydroxy-ethylamino)-hexyl]-carbamic acid benzyl ester (31.5 g; 0.107 moles), prepared as described in example 1, in a mixture of water (87 ml), 1N NaOH (17 ml) and ethyl acetate (180 ml), cooled at 0–5° C., controlling temperature and pH (about 8).

At the end of the dripping, the reaction mixture was kept under stirring for 30 minutes at 0–5° C., then the cooling was removed and further 1N NaOH (15 ml) was added, in order to bring again the pH at 8, then leaving under stirring at room temperature overnight. The phases were separated and the aqueous phase was extracted once again with ethyl acetate. The collected organic extracts were washed with brine, dried on sodium sulphate and concentrated under vacuum up to obtain an oily residue.

By chromatographical purification (eluant ethyl acetate: petrolatum from 60:40 to 70:30) 6-(benzyloxycarbonylamino-hexyl)-(2-hydroxy-ethyl)-carbamic acid benzyl ester (42.5 g; yield 92%) as an oil was obtained.

$^1$H-NMR (200 MHz, CDCl$_3$) δ(ppm): 7.39–7.25 (m, 10H, Ar); 5.10 and 5.07 (2s, 4H, 2COOCH$_2$); 3.71 (broad signal, 2H, *CH$_2$—OH); 3.43–3.01 (m, 4H, 2CH$_2$NCO); 1.57–1.19 (m, 8H, 4CH$_2$).

By working in a similar way the following compounds were obtained: (2-benzyloxycarbonylamino-ethyl)2-hydroxy-ethyl)-carbamic acid benzyl ester starting from 2-(2-aminoethylamino)-ethanol.

(yield 32%)

$^1$H-NMR (200 MHz, CDCl$_3$) δ(ppm): 7.33–7.28 (m, 10H, 2Ph); 5.06 and 5.04 (2s, 4H, 2CH$_2$—Ph); 3.73–3.34 (broad m, 8H, 4CH$_2$).

[2-(benzyl-benzyloxycarbonyl-amino)-ethyl]-(2-hydroxy-ethyl)carbamic acid benzyl ester starting from 2-[2-(benzylamino)-ethylamino-ethanol prepared as described in WO 96/18633.

(yield 50%)

$^1$H-NMR (200 MHz, CDCl$_3$) δ(ppm): (very broad signals) 7.42–7.13 (m, 15H, 3Ar), 5.12 and 5.09 (2s, 4H, COOCH$_2$*); 4.55 (s, 2H, N—*CH$_2$—Ph).

[242-hydroxy-ethoxy)-ethyl]-carbamic acid benzyl ester starting from 2-(2-aminoethoxy)-ethanol (yield 85%)

$^1$H-NMR (200 MHz, CDCl$_3$) δ(ppm): 7.36–7.28 (m, 5H, Ar); 5.18 (broad signal, 1H, NH); 5.08 (s, 2H, Ph—*CHO); 3.74–3.34 (m, 8H, *CH$_2$—*CH$_2$—O—*CH$_2$—*CH$_2$—OH); 2.13 (broad-t, 1H, OH).

EXAMPLE 3

Preparation of Methansulphonic Acid 2-[benzyloxycarbonyl-(6-benzyloxycarbonylaminohexyl)-amino-ethyl Ester Triethylamine (8.95 ml; 64.31 mmoles) was added to a solution of 6-(benzyloxycarbonylamino-hexyl)-(2-hydroxy-ethyl)-carbamic acid benzyl ester (13.78 g; 32.15 mmoles), prepared as described in example 2, in CH$_2$Cl$_2$ (140 ml). The mixture was cooled at 0–5° C. and then was dropwise added to a solution of methansulphonylchloride (3.36 ml, 43.41 mmoles) in CH$_2$Cl$_2$(20 ml).

At the end of the addition, the mixture was kept under stirring at room temperature for 60 minutes, then washed with 5% aqueous citric acid, with brine (20% NaCl), with 5% aqueous NaHCO$_3$ and finally with brine again. After drying on sodium sulphate and evaporation under vacuum methansulphonic acid 2-[benzyloxycarbonyl-(6-benzyloxycarbonylamino-hexyl)-amino]-ethyl ester (16.37 g; yield 100%) as a brown oil was obtained.

$^1$H-NMR (200 MHz, CDCl$_3$) δ(ppm): 7.35–7.27 (m, 10H, Ar); 5.11 and 5.07 (2s, 4H, 2COOCH$_2$); 4.36–4.19 (m, 2H, CH$_2$OSO$_2$); 3.57–3.51 (m, 2H, SO—CH$_2$—*CH$_2$N); 3.32–3.07 (m, 4H, 2CH$_2$N); 2.91 and 2.85 (2s-conformers, 3H, CH$_3$); 1.50–1.20 (m, 8H, 4CH$_2$).

By operating in a similar way the following compounds were obtained: methansulphonic acid 2-[2-(benzyloxycarbonyl-amino)-ethoxy]-ethyl ester starting from [2-(2-hydroxy-ethoxy)-ethyl]-carbamic acid benzyl ester, prepared as described in example 2.

(yield 98%)

$^1$H-NMR (200 MHz, CDCl$_3$) δ(ppm): 7.36–7.28 (m. 5H, Ar); 5.16 (broad signal, 1H, NH), 5.08 (s, 2H, COOCH$_2$); 4.34–4.30 (m, 2H, SO$_3$CH$_2$); 3.72–3.67 (m, 2H, SO$_3$—CH$_2$—*CH$_2$), 3.60–3.34 (m, 4H, N—*CH$_2$—*CH$_2$); 2.98 (s, 3H, SO$_3$CH$_3$).

Methansulphonic acid 2-[[2-(benzyl-benzyloxycarbonylamino)-ethyl]-benzyloxycarbonylamino]-ethyl ester starting from [2-benzyl-benzyloxycarbonyl-amino)-ethyl]-(2-hydroxy-ethyl)-carbamic acid benzyl ester, prepared as described in example 2.

(yield 72%)

$^1$H-NMR (200 MHz, CDCl$_3$) δ(ppm): 7.40–7.00 (m, 15H, 3Ar); 5.13–5.01 (broad signal, 4H, 2COOCH$_2$); 4.51–3.30 (broad-m, 10H, 4CH$_2$N and CH$_2$SO$_3$); 2.92–2.76 (broad signal, 3H, CH$_3$)

Methansulphonic acid 2-[benzyloxycarbonyl-(2-benzyloxycarbonylamino-ethyl)-amino]-ethyl ester starting from (2-benzyloxycarbonylamino-ethyl)-(2-hydroxy-ethyl)-carbamic acid benzyl ester, prepared as described in example 2.

(yield 100%)

$^1$H-NMR (200 MHz, CDCl$_3$) δ(ppm): 7.35–7.27 (m, 10H, 2Ar); 5.10 and 5.04 (2s, 4H, 2COOCH$_2$); 4.41–4.15 (m, 2H, *CH$_2$—MeSO$_2$); 3.63–3.23 (m, 6H, N—*CH$_2$—*CH$_2$—N—*CH$_2$); 2.90 (s-broad, 3H, MeSO$_2$).

EXAMPLE 4

Preparation of Erythromycin A Oxime N-oxide

A solution of H$_2$O$_2$ (72.00 g; titre 34% w/v; 0.72 moles) in water (780 ml) was dropwise added in 1 hour to a solution of erythromycin A oxime (35.00 g; 0.0467 moles) in methanol (1400 ml) under mechanical stirring, keeping the temperature at 20–25° C. At the end of the addition the reaction mixture was kept under stirring and at room temperature for 24 hours. After having added more H$_2$O$_2$ (8 ml), the mixture was kept under stirring for further 6 hours.

Methanol was evaporated under vacuum at a temperature of about 40° C. maintaining the volume of water constant (about 700 ml).

After filtering, washing with water and drying erythromycin A oxime N-oxide (36.3 g; yield 99%) was obtained as a white crystal solid.

$^1$H-NMR (200 MHz, DMSO-d$_6$) δ(ppm): 10.71–10.19 (broad signal, 2H, shifting H); 5.14–5.08 (m, 1H, H-13); 4.72 (d, 1H, J$_{HH}$=4.4 Hz, H-1"), 4.45 (d, 1H, J$_{HH}$=7.0 Hz, H-1').

EXAMPLE 5

Preparation of 3'-de(dimethylamino)-3',4'-dehydro-erythromycin A Oxime (Compound 1)

A solution of erythromycin A oxime N-oxide (30.00 g; 38.3 mmoles), prepared as described in example 4, in dimethylformamide (235 ml) was warmed at 150° C. in a pre-warmed oil bath (175–180° C.) and left at such temperature under mechanical stirring for 15–20 minutes.

After cooling and evaporation of dimethylformamide, the oily residue was collected with demineralized water (500 ml), warmed and cooled. The filtered solid was triturated and dried under vacuum at 40–45° C. furnishing a crude (25.5 g).

The crude was at first crystallized from acetonitrile (110 ml), filtered, washed with water and dried under vacuum at 50° C. obtaining a crystal product (20 g) which was crystallized again from methanol/water=65/35 (400 ml), filtered and dried under vacuum at 40–50° C.

Compound 1 as a crystal product was so obtained (10.3 g; yield 38.2%).

More product (3.7 g) was then recovered from the crystallization liquor with an overall yield of 51.8%.

$^1$H-NMR (200 MHz, CDCl$_3$) δ(ppm): 5.67–5.55 (m, 2H, *CH=*CH); 4.44 (d, 1H, J$_{HH}$=7.0 Hz, H-1'); 4.33–4.22 (m, 1H, H-5'); 4.13–4.04 (m, 1H-2'); 3.84–3.73 (m, 1H-8); 3.69 (s, 1H, H-11).

$^{13}$C-NMR (200 MHz, CDCl$_3$) δ(ppm): 171.11 (s, C-9), 132.2 and 126.1 (2s, C-3' and C-4').

EXAMPLE 6

Preparation of 3'-de(dimethylamino)-erythromycin A Oxime (Compound 2)

Platinum oxide (0.615 g) was added at room temperature to a solution of compound 1 (20.00 g; 28.4 mmoles), prepared as described in example 5, in ethanol (850 ml) (the complete dissolution was obtained after slight heating).

The mixture was hydrogenated in a Parr apparatus (1.36 atm) and the absorption was immediate.

After filtration of the catalyst and evaporation of the solvent under vacuum, the white crystal residue was triturated with petrolatum, filtered and dried under vacuum at 50° C. furnishing compound 2 (19.8 g; yield 99%).

$^1$H-NMR (200 MHz, CDCl$_3$) δ(ppm): 5.05–4.98 (m, 1H, H-13); 4.94 (d, 1H, J$_{HH}$=4.4 Hz, H-1"); 4.23 (d, 1H, J$_{HH}$=7.4 Hz, H-1'); 3.44–3.30 (m, 1H, H-2'); 2.07–1.21 (m, 2H, H-3'), 1.65–1.45 (m, 2H, H-4').

$^{13}$C-NMR (200 MHz, CDCl$_3$) δ(ppm): 171.2 (s, C-9); 104.7 (s, C-1'), 31.8 (s, C-3'); 29.5 (s, C-4').

EXAMPLE 7

Preparation of 3'-de(dimethylamino)-erythromycin A (E)-9-[O-[2-[benzyloxy-carbonyl-(6-benzyloxy-carbonylamino-hexyl)-amino]-ethyl]-oxime] (Compound 3)

Compound 2 (12.51 g; 17.73 mmoles), prepared as described in example 6, was added to a 95% solution of potassium tert-butylate (2.45 g; 19.48 mmoles) in anhydrous THF (120 ml), under stirring and in a nitrogen atmosphere, maintaining the temperature at about 25° C.

The reaction mixture was kept under stirring for 30 minutes at room temperature and then 18-crown-6 ether (4.69 g; 17.73 mmoles) and a solution of methansulphonic acid 2-[benzyloxycarbonyl-(6-benzyloxycarbonylamino-hexyl)-amino]-ethyl ester (8.98 g; 17.73 mmoles), prepared as described in example 3, in anhydrous THF (60 ml), were added, leaving under stirring at room temperature overnight.

After evaporation of the solvent under vacuum, the residue was taken up with a mixture of ethyl acetate and brine (20% NaCl) and the phases were separated. The aqueous phase was again extracted with ethyl acetate. The collected and dried organic extracts were concentrated under vacuum obtaining a crude (23.4 g).

By chromatographycal purification (eluant CH$_2$Cl$_2$:CH$_3$OH=97:3) still slightly impure compound 3 was obtained (15.42 g), which was used without further purifications.

H-NMR (200 MHz, CDCl$_3$) δ(ppm): 7.35–7.28 (m, 10H, Ar); 5.14–5.06 (m, 1H, H-13); 5.11 and 5.07 (2s, 4H, 2COOCH$_2$); 4.84 (d, 1H, J$_{HH}$=4.4 Hz, H-1'); 4.28 (d, 1H, J$_{HH}$=7.4 Hz, H-1').

By working in a similar way the following compounds were obtained: 3'-de(dimethylamino)-erythromycin A (E)-9-[O-[2-[2-(benzyloxycarbonylamino)-ethoxy]-ethyl]-oxime] (Compound 4) from methansulphonic acid 2-[2-(benzyloxycarbonyl-amino)-ethoxy]-ethyl ester.

(yield 62%)

$^1$H-NMR (200 MHz, CDCl$_3$) δ(ppm): 7.34–7.27 (m, 5H, Ar); 6.09 (broad signal, 1H, NH); 5.13–5.05 (m, 1H, H-13); 5.06 (s, 2H, COOCH$_2$) 4.79 (d, 1J$_{HH}$=4.4 Hz, H-1'); 4.26 (d, 1H, J$_{HH}$=7.4 Hz, H-1').

3'-de(dimethylamino)-erythromycin A (E)-9-O-[2-methoxy-ethoxy]-methyl]-oxime](Compound 5 from methoxy-ethoxy-methyl chloride.

(yield 32.5%)

$^1$H-NMR (200 MHz, CDCl$_3$) δ(ppm): 5.21–5.12 (m, 2H, O—CH$_2$—O); 5.12–5.05 (m, 1H, H-13); 4.85 (d, 1H, J$_{HH}$=5.4 Hz, H-1"); 4.39 (d, 1H, J$_{HH}$=7.5 Hz, H-1'); 3.40 (s, 3H, CH$_2$—O—*CH$_3$); 3.27 (s, 3H, H-3").

$^{13}$C-NMR (200 MHz, CDCl$_3$) δ(ppm): 172.5 (s, C-9); 97.44 (s, NO—C—O); 32.12 (s, C-3"); 29.84 (s, C-4').

3'-de(dimethylamino)-erythromycin A (E)-9-[O-[2-[[2-(benzyl-benzyloxycarbonyl-amino)-ethyl]-benzyloxycarbonyl-amino]-ethyl]-oxime] (Compound 12) from methansulphonic acid 2-[[2-(benzyl-benzyloxycarbonyl-amino)-ethyl]-benzyloxycarbonyl-amino]-ethyl ester $^1$H-NMR (200 MHz, CDCl$_3$) δ(ppm): 7.40–7.16 (broad m., 15H, 3Ph); 5.17–5.00 (m, 5H, 2*CH$_2$—Ph and H-13).

3-de(dimethylamino)-erythromycin A (E)-9-[O-[2-[[2-(benzyloxycarbonyl-amino)-ethyl]-benzyloxycarbonyl-amino]-ethyl]-oxime] (Compound 13) from methansulphonic acid 2-[benzyloxycarbonyl-(2-benzyloxycarbonylamino-ethyl)-amino]-ethyl ester (yield 42%)

$^1$H-NMR (200 MHz, CDCl$_3$) δ(ppm): 7.38–7.25 (m, 10H, 2Ph); 5.11 and 5.05 (2s, 4H, 2COOCH$_2$); 5.14–5.00 (m, 1H, H-13); 4.89–4.79 (broad-m, 1H, H-1"); 2.26 (d, 1H, J$_{HH}$=7.4 Hz, H-1').

EXAMPLE 8

Preparation of 3'-de(dimethylamino)-erythromycin A (E)-9-[O-[2-[(6-amino-hexyl)-amino]-ethyl]-oxime] (Compound 6)

10% Pd/C (1.6 g) was added to a solution of compound 3 (15.42 g; 13.8 mmoles), obtained as described in example 7, in ethanol (160 ml).

The mixture was hydrogenated in a Parr apparatus (1.02 atm). After 2 hours the catalyst was filtered and the solvent was evaporated.

The residue was purified by flash chromatography (eluant CH$_2$Cl$_2$:CH$_3$OH:NH$_3$=85:15:1.5 then 80:20:2) furnishing compound 6 (8.48 g) as an amorphous white solid.

$^1$H-NMR (200 MHz, CDCl$_3$) δ(ppm): 5.07–5.00 (m, 1H, H-13); 4.79 (d, 1H, J$_{HH}$=4.4 Hz, H-1"); 4.21 (d, 1H, J$_{HH}$=7.4 Hz, H-1').

$^{13}$C-NMR (200 MHz, CDCl$_3$) δ(ppm): 171.8 (s, C-9); 71.6 (s, =N—O—C); 49.43 and 49.0 (2s, =N—O—C—*C—N—*C), 41.1 (s, C—NH$_2$).

By working in a similar way the following compounds were obtained:

3'-de(dimethylamino)-erythromycin A (E)-9-[O-[2-(2-amino-ethoxy)-ethyl]-oxime] (Compound 7) starting from compound 4

(yield 85%)

¹H-NMR (200 MHz, CDCl₃) δ(ppm): 5.12–5.05 (m, 1H, H-13); 4.83 (d, 1H, $J_{HH}$=4.4 Hz, H-1"); 4.26 (d, 1H, $J_{HH}$=7.5 Hz, H-1').

3'-de(dimethylamino)-erythromycin A (E)-9-[O-[2-[(2-benzylamino-ethyl)-amino]-ethyl]-oxime] (Compound 4) starting from compound 12

(yield 48%)

¹H-NMR (200 MHz, CDCl₃) δ(ppm): 7.32–7.17 (m, 5H, Ph); 5.08–5.00 (m, 1H, H-13); 4.74 (d, 1H, $J_{HH}$=4.6 Hz, H-1"); 4.22 (d, 1H, $J_{HH}$=7.4 Hz, H-1'); AB system: Va=3.80, Vb=3.76, Jab=13.7 Hz,*CH₂Ph.

¹³C-NMR (200 MHz, CDCl₃) δ(ppm): 171.3 (s, C-9); 105.0 (s, C-1'); 32.2 (s, C-3'); 29.8 (s, C-4').

3'-de(dimethylamino)-erythromycin A (E)-9-[O-[2-[(2-amino-ethyl)-amino]-ethyl]-oxime] (Compound 15) starting from compound 13

(yield 70%)

¹H-NMR (200 MHz, CDCl₃) δ(ppm): 5.08–5.00 (m, 1H, H-13); 4.76 (d, 1H, $J_{HH}$=4.6 Hz, H-1"); 4.23 (d, 1H, $J_{HH}$=7.4 Hz, H-1').

EXAMPLE 9

Preparation of 3'-de(dimethylamino)-erythromycin A (E)-9-[O-[2-[6-[(thiazol-2-ylmethyl)-amino]-hexyl-amino]-ethyl]-oxime] (Compound 8)

A suspension of compound 6 (3 g; 3.53 mmoles), prepared as described in example 8, 97% 2-thiazolecarbaldehyde (0.412 g; 3.53 mmoles) and molecular sieves (3 Å, 6.75 g) in ethanol (60 ml) was left under stirring for 3 hours.

After filtering the molecular sieves on celite, 10% Pd/C (0.3 g) was added and the mixture was hydrogenated in a Parr hydrogenator (1.02 atm). After 20 hours the catalyst was filtered and the solvent evaporated.

By chromatografical purification of the residue (eluant CHCl₃:petrolatum:triethylamine=90:10:10) compound 8 was obtained (1.66 g; yield 49.8%) as a amorphous solid.

¹H-NMR (200 MHz, CDCl₃) δ(ppm): 7.66 (d, 1H, $J_{HH}$= 3.2 Hz, CHN); 7.22 (d, 1H, CHS); 5.08–5.02 (m, 1H, H-13); 4.78 (d, 1H, $J_{HH}$=4.4 Hz, H-1"); 4.21 (d, 1H, $J_{HH}$=7.4 Hz, H-1'); 4.07 (s, 2H, *CH₂-thiaz.).

¹³C-NMR (200 MHz, CDCl₃) δ(ppm): 172.0 (s, S—C=N); 171.7 (s, C-8), 142.4 (s, CHN); 118.7 (s, CHS); 104.9 (s, C-1'); 96.3 (s, C-1"); 71.7 (s, N—O—C).

By working in a similar way the following compounds were obtained:

3'-de(dimethylamino)erythromycin A (E)-9-[O-[2-[6-(benzylamino)-hexylamino]-ethyl]-oxime] (Compound 9) from compound 6 and benzaldehyde ¹H-NMR (200 MHz, CDCl₃) δ(ppm): 7.27–7.17 (m, 5H, Ar); 5.07–5.01 (m, 1H, H-13); 4.75 (d, 1H, $J_{HH}$=4.4 Hz, H-1"); 4.19 (d, 1H, J=7.4 Hz, H-1'); 3.73 (s, 2H, *CH₂—Ph).

¹³C-NMR (200 MHz, CDCl₃) δ(ppm): 171.8 (s, C-9); 104.9 (s, C-1'); 96.3 (s, C-1"); 71.8 (s, =N—O—C); 53.8 (s, N—*C—Ph); 49.7, 49.2 and 49.1 (3s, 3N—C).

3'-de(dimethylamino)-erythromycin A (E)-⁹-[O-[2-[2-[(thiazol-2-ylmethyl)-amino]-ethoxy]-ethyl]-oxime] (Compound 10) from compound 7 and 2-thiazolecarbaldehyde.

¹H-NMR (200 MHz, CDCl₃) δ(ppm): 7.64 (d, 1H, $J_{HH}$= 3.2 Hz, CHN); 7.19 (d, 1H, CHS); 5.10–5.02 (m, 1H-13); 4.78 (d, 1H, $J_{HH}$=4.4 Hz, H-1"); 4.21 (d, 1H, $J_{HH}$=7.4 Hz, H-1'); 4.13 (s, 2R, *CH₂-thiaz.).

³C-NMR (200 MHz, CDCl₃) δ(ppm): 172.7 (s, SC=N), 171.5 (s, C-9); 142.4 (s, CHN'); 118.6 (s, CHS); 104.7 (s, C-1'); 96.4 (s, C-1"); 50.7 (s, N—*C-thiaz.).

3'-de(dimethylamino)-erythromycin A (E)-9-[O-[2-[2-(benzylaminol)-ethoxy]-ethyl]-oxime] (Compound 11) from compound 7 and benzaldehyde.

¹H-NMR (200 MHz, CDCl₃) δ(ppm): 7.33–7.10 (m, 5H, Ar); 5.12–5.04 (m, 1H, H-13); 4.78 (d, 1H, $J_{HH}$=4.4 Hz, H-1"); 4.72 (d, 1H, $J_{HH}$=7.4 Hz, H-1'); 3.80 (s, 2H, NCH₂).

³C-NMR (200 MHz, CDCl₃) δ(ppm): 171.5 (s, C-9); 104.8 (s, C-1'); 96.5 (s, C-1'); 69.4, 70.8 and 72.4 (3s, 3OCH₂); 53.6 (s, *C—Ph); 48.2 (s, O—C—*C—N).

3'-de(dimethylamino)-erythromycin A (E)-9-[O-[2-[2-[(thiazol-2-ylmethyl)-amino]-ethyl-amino]-ethyl]-oxime] (Compound 16) from compound 15 and 2-thiazolecarbaldehyde.

¹H-NMR (200 MHz, CDCl₃) δ(ppm): 7.62 (d, 1H, JHH= 3.0 Hz, N—*CH=CH); 7.18 (d, 1H, S—*CH=CH); 4.18 (d, 1H, JHH=7.4 Hz, H-1').

¹³C-NMR (200 MHz, CDCl₃) δ(ppm): 172.6 (s, SC=N); 171.3 (s, C-9); 142.4 (s, CHN); 118.6 (s, CHS); 104.9 (s, C-1'); 96.4 (s, C-1"); 32.17 (s, C-3'); 29.8 (s, C-4').

3'-de(dimethylamino)-erythromycin A (E)-9-[O-[2-[6-[(2-phenyl-1H-1H-imidazol-4-ylmethyl)-amino]-hexyl-amino]-ethyl]-oxime] (Compound 17) from compound 6 and 2-phenyl-1H-imidazole-4carbaldehyde.

¹H-NMR (200 MHz, CDCl₃) δ(ppm): 7.86–7.21 (m, 5H, Ar); 6.91 (s, 1H, CH-Imid.); 5.11–5.02 (m, 1H-13); 4.76 (d, 1H, JHH=4.2 Hz, H1"); 4.21 (d, 1H, JHH=7.4 Hz, H1'); 3.76 (s, 2H,*CH₂-Imid.); 3.23 (s, 3H, OMe).

¹³C-NMR (200 MHz, CDCl₃) δ(ppm): 171.7 (s, C-9); 104.8 (s, C-1'); 96.3 (s, C-1'); 32.1 (s, C-3'); 29.9 (s, C-4').

3'-de(dimethylamino)-erythromycin A (E)-9-[O-[2-[6-[(1-methyl-2-phenyl-1H-1H-imidazol-4-ylmethyl)-amino]-hexyl-amino]-ethyl]-oxime] (Compound 18) from compound 6 and 1-methyl-2-phenyl-1H-1-imidazole-4-carbaldehyde.

¹H-NMR (200 MHz, CDCl₃) δ(ppm): 7.57–7.31(m, 5H, Ar); 6.87 (s, 1H, CH-Imid.); 5.09–5.00 (m, 1H-13); 4.76 (d, 1H, JHH=4.2 Hz, H1"); 4.20 (d, 1H, JHH=7.4 Hz, H1'); 3.71 (s, 2H,*CH₂-Imid.); 3.62 (s, 3H, NMe); 3.21 (s, 3H, OMe).

¹³C-NMR (200 MHz, CDCl₃) δ(ppm): 171.8 (s, C-9); 104.9 (s, C-1'); 96.3 (s, C-1"); 32.1 (s, C-3'); 29.7 (s, C-4').

EXAMPLE 10

Preparation of 3'-de(dimethylamino)-erythromycin A (E)-9-[O-[2-[2-[(thiazol-2-ylmethyl)-(methyl)-amino]-ethoxy]-ethyl]oxime] (Compound 19)

Compound 10 (0.23 g; 0.258 mmoles), formaldehyde (37% w/v; 42 μl; 0.516 mmoles), 10% Pd on charcoal (25 mg) and a 4:1 mixture of ethanol and water (10 ml) were charged in a Parr apparatus at 1.02 atm. After 2 and 3 hours further formaldehyde was added (42 μl+21 μl) At the end of the reaction (overall 6 hours) the catalyst was filtered off and the solvent was evaporated. The resultant residue was purified by flash chromatography (eluant CH₂Cl₂:CH₃OH=95:5) furnishing compound 19 as an amorphous solid.

¹H-NMR (200 MHz, CDCl₃) δ(ppm): 7.64 (d, 1H, JHH= 3.6 Hz, N—*CH=CH); 7.21 (d, 1H, S—*CH=CH);

5.10–5.00 (m, 1H, H-13); 4.80 (d, 1H, JHH=4.6 Ha, H1″); 4.23 (d, 1H, JHH=7.4 Hz, H1'); 3.94 (s, 2H,*CH$_2$-Thiaz.).

$^{13}$C-NMR (200 MHz, CDCl$_3$) δ(ppm): 172.0 (s, SC=N), 171.8 (s, C-9), 142.2 (s, CHN); 119.3 (s, CHS); 104.9 (s, C-1'); 96.4 (s, C-1″); 32.2 (s, C-3'); 29.9 (s, C-4').

EXAMPLE 11

In vitro Pharmacological Activity

A) Release of Interleukin 8 (IL-8)

A human endothelial immortalized cell line (ECV304) was obtained from ATTC (Rockville, Md.) and grown in Medium 199, mod. Earle's salts (GIBCO, Life Technologies, Grand Island, N.Y.), supplemented with 20% Fetal Calf Serum (GIBCO), 100 U/ml of penicillin and 100 □g/ml of streptomycin (SIGMA, St. Louis, Mo.) in wet atmosphere with 5% CO$_2$ at 37° C.

The cells were cultivated on 96 well plates up to obtain a confluent monolayer. The compounds to be evaluated were dissolved in DMSO at 10$^{-2}$M and diluted with culture medium.

The compounds were pre-incubated with the cells 1 hour before the challenge.

The release of IL-8 was induced by adding 0.66 □g/ml of lipopolysaccharide B (*E. coli* 055:B5, Difco, Detroit, Mich.) in a final volume of 200 □l.

After one night, the supernatant was collected for the IL-8 test.

The specific immunoreactivity for IL-8 in the culture supernatant was measured with ELISA kit (Amersham, UK).

Results were expressed as the highest obtainable inhibition (efficacy) and, whether possible, as the concentration at which 50% of such effect (TC$_{50}$) is obtained.

B) Release of Superoxide Anions

Neutrophils were separated from venous blood of healthy volunteers by centrifugation on Ficoll-Hypaque, followed by sedimentation on 6% dextrane and osmotic lysis of erythrocytes. Neutrophils were then washed and resuspended in a medium made of RPMI-1640 supplemented with 5% foetal calf serum and 1.34 mmoles/l of disodium dihydrate EDTA. The cells were maintained for 24 hours at 4° C. and before the test the suspension was centrifugated and resuspended in HBSS (Hanks' balanced salt solution). The vitality and the purity of the neutrophil preparation was verified by dyeing with Trypan blue and Turk blue.

The superoxide anions were measured by using Lucigenin (bis-N-methylacridinium nitrate)-enhanced chemiluminescence technique.

Neutrophils (2×10$^6$ cells/ml) were pre-incubated for 30 minutes at 37° C. in 900 □l of HBSS with and without the tested compound (reading system).

The production of superoxide anions was measured with a Lumac/3M bio-counter after addition of 100 □l of a solution in HBSS of Lucigenin (2 mmoles/l) and N-formyl-L-methionyl-L-leucyl-L-phenylalanine (FLMP) as stimulating agent at the concentration of 1×10$^5$ M to the reading system. FLMP was dissolved in DMSO (1×10$^{-2}$ M) and further diluted in HBSS. The compound to be tested was dissolved in DMSO at the concentration of 10$^{-2}$ M. Lower concentrations, in DMSO, were prepared from that solution, and tested. The DMSO amount present in the reading system was lower than 1%.

The luminosity values obtained at the peak, for each tested concentration of the compound, were transformed in inhibition percentage in comparison with the reference.

The concentration able to inhibit the production of superoxide anion at 50% (IC$_{50}$) was calculated from the obtained "dose-response" curve.

In the following table the results obtained for some compounds of formula I representing the all class in comparison with erythromycin, clarithromycin and roxithromycin are reported.

TABLE 1

In vitro inhibition of IL-8 release, expressed as potency (IC$_{50}$) and as efficacy (%), and of superoxide anion release (IC$_{50}$).

| Compound | IL-8 release | | O$_2$ release IC$_{50}$ μM |
|---|---|---|---|
| | potency IC$_{50}$ μM | efficacy (%) | |
| 1 | — | 29 | 35.3 ± 5.4 |
| 2 | — | 29 | 11.4 ± 2.9 |
| 5 | 12 | 55 ± 0.9 | >100 |
| 6 | 7.7 ± 0.3 | 37 ± 10 | 9.9 ± 0.69 |
| 8 | — | 19 ± 1 | 3.5 ± 0.2 |
| 9 | — | — | 3.5 ± 0.5 |
| 11 | — | 22 ± 4 | 5 |
| 16 | — | 35 | 14.3 |
| clarithromycin | 8.9 ± 3.2 | 48 ± 6 | 49.2 ± 1.9 |
| erythromycin | — | 27 ± 1 | >100 |
| roxithromycin | 5.5 ± 1.5 | 43 ± 6 | 89 ± 5 |

EXAMPLE 12

In vivo Pharmacological Activity

Animals

Male Sprague-Dawley rats weighing between 200 and 300 g were used.

The rats used in the experiments were not evidently infected. The animals were maintained in standard conditions for 7 days before being sacrificed.

Endotoxin Administration

LPS (*E. coli* lipopolisaccharide) (endotoxin; 055:B5 serum-type; Sigma Chemical Co., St. Louis, Mo.) was dissolved in saline sterile solution and was administered by intraperitoneal injection (i.p.) at a dose of 6 mg/kg (1 ml/kg). Analogously the saline solution and/or the carrier (saline solution+0.5% Tween 20) were injected into the control animals.

Compound Administration (Prophylactic Treatment)

Each compound was administered by i.p. injection twice a day for 6 days, the 7$^{th}$ day 1 hour before and 5 hours after LPS administration. The compounds were suspended with 0.5% Tween 20 in the saline solution.

Bronchoalveolar Lavage

After 24 hours from the LPS injection rats were sacrificed with an overdose of nembutal (100 mg/kg i.p.). The trachea was incannulated and the lung was washed by instilling two 5 ml aliquots of PBS (phosphate buffer saline) at 37° C. and the fluid was immediately removed. The fluid was again injected and the procedure was altogether repeated three times for each aliquot.

Cell Counting and Differentiation

200 μl of BALF (bronchoalveolar lavage fluid) were diluted in 1 ml of cold water and 19 ml of Isoton. The overall number of cells was counted twice by using Contraves autolyser 800. When the total number was lower than 2000, BALFs were centrifugated at 800 rpm for 10 minutes in order to separate the cells from the supernatant. The supernatants were discharged and the cells resuspended in a small amount of PBS. For the cytological evaluation, 50 μl of the solution with the resuspended cells were centrifugated for 1 minute at 1300 rpm by using a Shandon Cytospin centrifuge. The slides were fixed in acetone and dyed with DiffQuick. The differential counts of cells were performed on each slide by counting 200 cells at random; cellular types were classified as neutrophils, eosinophils and mononuclear cells according to morphological standard criteria.

In the following table the results obtained with some compounds of formula I representative of the all class are reported.

TABLE 2

In vivo inhibition of neutrophilia induced by LPS after repeated administrations.

| Compound | Inhibition (%) |
|---|---|
| 2 | −31 |
| 6 | −11 |
| 9 | −96 |
| erythromycin | −46 |
| clarithromycin | −47 |
| roxithromycin | −50 |

What is claimed is:

1. A compound of formula

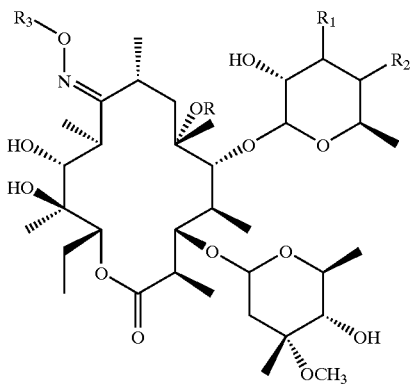

(I)

wherein

R is hydrogen or methyl;

$R_1$ and $R_2$ are both hydrogen or they together form a bond;

$R_3$ is hydrogen, a linear or branched $C_1$–$C_5$ alkyl group, a benzyl group, optionally substituted by one or more substituents selected among nitro groups, hydroxy groups, carboxylic groups, amino groups, linear or branched $C_1$–$C_5$ alkyl groups, $C_1$–$C_4$ alkoxycarbonyl groups, aminocarbonyl groups or ciano groups, or a chain of formula

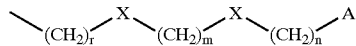

wherein

A is hydrogen or a phenyl group optionally substituted by one or two substituents selected among nitro groups, hydroxy groups, carboxylic groups, amino groups, linear or branched $C_1$–$C_5$ alkyl groups, $C_1$–$C_4$ alkoxycarbonyl groups, aminocarbonyl groups or ciano groups, or a 5 or 6 membered heterocycle, sated or unsaturated, containing from 1 to 3 heteroatoms selected among nitrogen, oxygen and sulphur, optionally substituted by one or two substituents selected among $C_1$–$C_5$ alkyl groups, phenyl groups, hydroxy groups, oxo (=O) groups, nitro groups, $C_1$–$C_4$ alkoxycarbonyl groups, aminocarbonyl groups, mono or di-$C_1$–$C_4$-alkylaminocarbonyl groups, $C_1$–$C_4$-alkylcarbonyl groups;

X and Y, the same or different, are O, S, SO, $SO_2$ or $NR_4$, in which $R_4$ is hydrogen, a linear or branched $C_1$–$C_5$ alkyl group, a $C_1$–$C_5$ alkoxycarbonyl group, a benzyloxycarbonyl group;

r is an integer from 1 to 6;

m is an integer from 1 to 8;

n is an integer from 0 to 2;

and their pharmaceutically acceptable salts;

the compounds 3'-desdimethylamino-3',4'-dehydroerythromycin A oxime and 3'-desdimethylamino-3',4'-dehydroerythromycin A 9-O-methyloxime being excluded.

2. The compound according to claim 1, wherein R, $R_1$ and $R_2$ are hydrogen.

3. The compound according to claim 2, wherein $R_3$ is a chain of formula

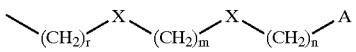

wherein

A is hydrogen or a phenyl group optionally substituted by one or two substituents selected among nitro groups, hydroxy groups, carboxylic groups, amino groups, linear or branched $C_1$–$C_5$ alkyl groups, $C_1$–$C_4$ alkoxycarbonyl groups, aminocarbonyl groups or ciano groups, or a 5 to 6 membered heterocycle, saturated or unsaturated, containing from 1 to 3 heteroatoms selected among nitrogen, oxygen and sulphur, optionally substituted by one or two substituents selected among $C_1$–$C_5$ alkyl groups, phenyl groups, hydroxy groups, oxo (=O) groups, nitro groups, $C_1$–$C_4$ alkoxycarbonyl groups, aminocarbonyl groups, mono or di-$C_1$–$C_4$-alkylaminocarbonyl groups, $C_1$–$C_4$-alkylcarbonyl groups;

X and Y, the same or different, are O, S, SO, $SO_2$ or $NR_4$, in which $R_4$ is hydrogen, a linear or branched $C_1$–$C_5$ alkyl group, a $C_1$–$C_5$ alkoxycarbonyl group, a benzyloxycarbonyl group;

r is an integer from 1 to 6;

m is an integer from 1 to 8;

n is an integer from 0 to 2;

and their pharmaceutically acceptable salts;

the compounds 3'-desdimethylamino-3',4'-dehydroerythromycin A oxime and 3'-desdimethylamino-3',4'-dehydroerythromycin A 9-O-methyloxime being excluded.

4. The compound according to claim 2, wherein $R_3$ is a chain of formula

wherein r is 2, m is 2 or 6, n is 1, Y is $NR_4$, X is O or $NR_4$, $R_4$ is hydrogen and A is phenyl or thiazolyl.

5. A pharmaceutical composition comprising, at least one compound according to claim 1 and a pharmaceutically acceptable carrier.

6. A method of inhibiting, arresting, or reducing inflammatory diseases comprising administering the at least one compound according to claim 1 to a human being or an animal in need thereof.

7. A method of treating, inhibiting, arresting, or reducing symptoms of inflammatory diseases comprising administering the at least one compound according to claim 1 to a human being or an animal in need thereof.

8. A method of inhibiting, arresting, or reducing inflammatory diseases comprising administering the at least one compound selected from the group consisting of 3'-desdimethylamino-3',4'-dehydroerythromycin A 9-O-methyloxime and 3'desdimethylamino-3',4'-dehydroerythromycin A 9-O-oxime to a human being or an animal in need thereof.

9. A method of treating, inhibiting, arresting, or reducing symptoms of inflammatory diseases comprising administering the at least one compound selected from the group consisting of 3'-desdimethylamino-3',4'-dehydroerythromycin A 9-O-methyloxime and 3'desdimethylamino-3',4'-dehydroerythromycin A 9-O-oxime to a human being or an animal in need thereof.

10. A process of making a pharmaceutical composition, comprising mixing at least one compound according to claim 1 with a pharmaceutically acceptable carrier.

* * * * *

UNITED STATES PATENT AND TRADEMARK OFFICE
CERTIFICATE OF CORRECTION

PATENT NO. : 6,455,576 B1
DATED : September 24, 2002
INVENTOR(S) : Pellacini et al.

It is certified that error appears in the above-identified patent and that said Letters Patent is hereby corrected as shown below:

<u>Title page,</u>
Item [73], Assignee should read:
-- [73] Assignee: Zambon Group S.p.A., Vicenza (IT) --
Item [22], the PCT filing date should read:
-- [22] PCT Filed: Jan. 12, 2000 --
Item [30], Foreign Application Priority Data should read:
-- [30]          Foreign Application Priority Data
Jan. 15, 1999  (IT) ………………………….. MI99A000061 --

Signed and Sealed this

Twenty-first Day of January, 2003

JAMES E. ROGAN
*Director of the United States Patent and Trademark Office*